(12) United States Patent
Desinger

(10) Patent No.: US 7,666,183 B2
(45) Date of Patent: Feb. 23, 2010

(54) ELECTRODE ARRANGEMENT FOR SURGICAL INSTRUMENT

(75) Inventor: Kai Desinger, Berlin (DE)

(73) Assignee: Celon AG Medical Instruments (DE)

( * ) Notice: Subject to any disclaimer, the term of this patent is extended or adjusted under 35 U.S.C. 154(b) by 787 days.

(21) Appl. No.: 10/296,189

(22) PCT Filed: May 22, 2001

(86) PCT No.: PCT/EP01/05879

§ 371 (c)(1), (2), (4) Date: Apr. 23, 2003

(87) PCT Pub. No.: WO01/89403

PCT Pub. Date: Nov. 29, 2001

(65) Prior Publication Data

US 2004/0116923 A1 Jun. 17, 2004

(30) Foreign Application Priority Data

May 26, 2000 (DE) .............................. 200 09 426 U

(51) Int. Cl.
*A61B 18/18* (2006.01)
(52) U.S. Cl. .............................. 606/50; 606/41; 606/48
(58) Field of Classification Search .............. 606/20–52
See application file for complete search history.

(56) References Cited

U.S. PATENT DOCUMENTS

| | | | |
|---|---|---|---|
| 3,987,795 A | 10/1976 | Morrison | |
| 4,207,897 A * | 6/1980 | Lloyd et al. | 606/23 |
| 4,381,007 A | 4/1983 | Doss | |
| 5,078,713 A * | 1/1992 | Varney | 606/23 |
| 5,281,213 A * | 1/1994 | Milder et al. | 606/15 |
| 5,281,215 A * | 1/1994 | Milder | 606/20 |
| 5,334,193 A | 8/1994 | Nardella | |
| 5,647,871 A | 7/1997 | Levine | |
| 5,662,680 A | 9/1997 | Desai | |
| 5,688,267 A * | 11/1997 | Panescu et al. | 606/41 |
| 5,891,095 A * | 4/1999 | Eggers et al. | 604/114 |
| 5,951,546 A | 9/1999 | Lorentzen | |
| 5,993,446 A | 11/1999 | Sutter | |
| 6,033,398 A | 3/2000 | Farley | |
| 6,102,046 A * | 8/2000 | Weinstein et al. | 128/898 |
| 6,110,169 A | 8/2000 | Mueller | |
| 6,379,349 B1 | 4/2002 | Mueller | |

FOREIGN PATENT DOCUMENTS

| | | |
|---|---|---|
| WO | WO 96/34569 A1 | 11/1996 |
| WO | WO 96/17009 A2 | 5/1997 |
| WO | WO 00/36985 A2 | 6/2000 |

* cited by examiner

*Primary Examiner*—Roy D Gibson
(74) *Attorney, Agent, or Firm*—Hahn Loeser & Parks LLP

(57) ABSTRACT

The invention concerns an electrode arrangement for a surgical instrument for the electrothermal coagulation of human or animal tissue, comprising an elongate carrier, at least two electrodes which extend in the longitudinal direction of the carrier and which are connectable to an external ac voltage, and a plurality of self-supporting metal bar profile members which extend in the longitudinal direction of the carrier and which are connected together by means of one or more insulating spacer elements and form the electrodes. It is achieved in that at least one bar profile member is in the form of a hollow profile member or a solid profile member.

22 Claims, 3 Drawing Sheets

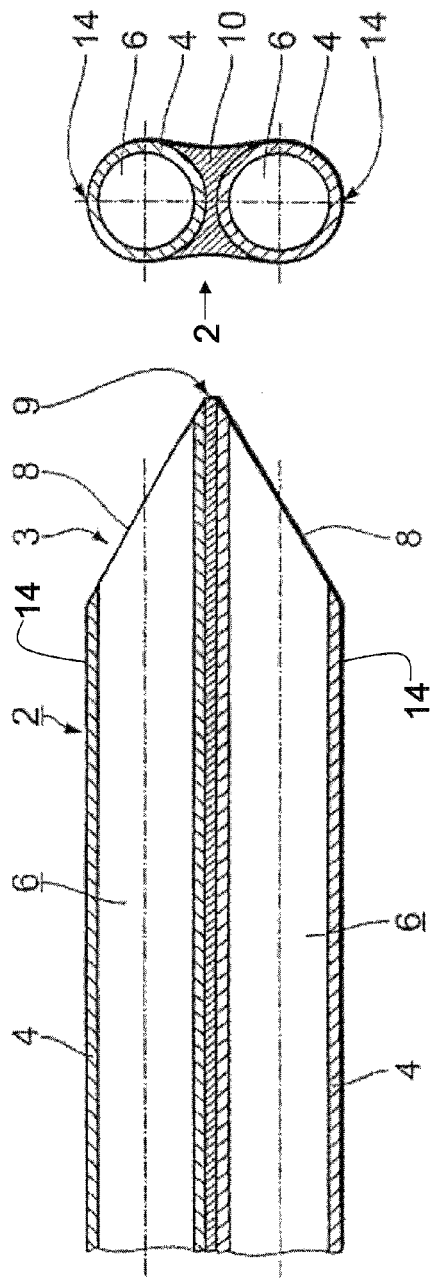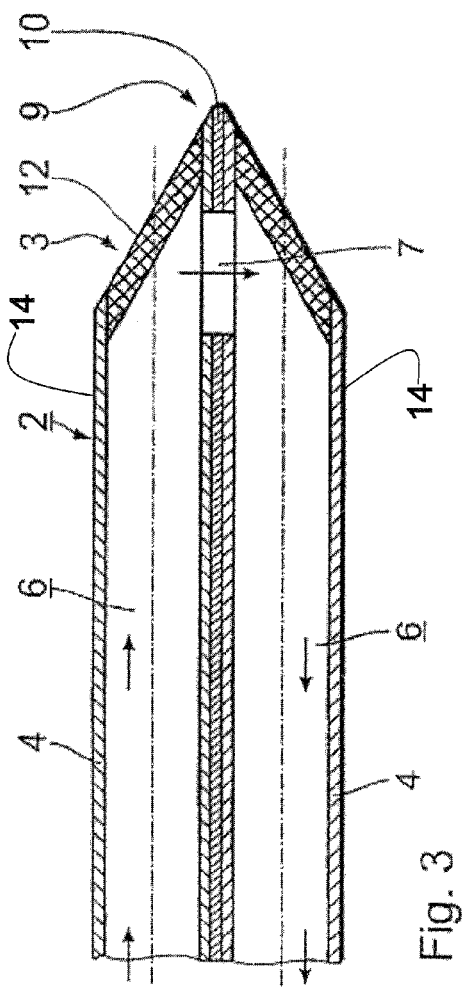
Fig. 1  Fig. 2  Fig. 3

ELECTRODE ARRANGEMENT FOR SURGICAL INSTRUMENT

The invention concerns an electrode arrangement for a surgical instrument for the electrothermal coagulation of human or animal tissue, comprising an elongate carrier, at least two electrodes which extend in the longitudinal direction of the carrier and which are connectable to an external ac voltage, and a plurality of self-supporting metal bar profile members which extend in the longitudinal direction of the carrier and which are connected together by means of one or more insulating spacer elements and form the electrodes.

BACKGROUND OF THE ART

The use of high-frequency alternating currents (for example in the frequency range of between 300 KHz and 2 MHz) to produce high temperatures for tissue coagulation and for tissue division has already long been known in surgery. In practice so-called monopolar electrode arrangements or bipolar electrode arrangements are used to introduce the HF-current into the tissue.

In the monopolar arrangements an electrode—also referred to as the neutral electrode—is in the form of a large-area electrode which is applied in the proximity of the treatment location to the skin of the patient and fixed there and grounded, or connected to ground. A second electrode which is handled by the operator—also referred to as the active electrode—is connected to the ac voltage source. The electrode is adapted in respect of its shape to the respective use, in particular to the size of the tissue region to be treated, in such a way that both the operating time and also the thermal loading of the body region or organ in question are reasonable and only coagulate the desired region of tissue.

In arrangements for bipolar HF-thermotherapy both electrodes are connected to a HF-generator and are of dimensions which are established in conjunction with each other, arranged for example on an insulating elongate carrier, and are placed by the operator in the immediate proximity of the parts being treated and are generally also actively guided.

PCT application WO 97/17009 discloses a bipolar electrode arrangement with a flushing passage by way of which flushing fluid can be introduced into the intervention region. Two or three electrodes are arranged in the form of a portion of a cone on a conical distal tip of the instrument, which can be inserted into the tissue, in which case the electromagnetic HF-field is formed between the electrodes and is intended to coagulate the surrounding tissue.

PCT application WO 96/34569 and the publications referred to in the related international search report disclose systems and processes for the coagulation of body tissue and observing a pre-calculated maximum tissue temperature, in which fluid cooling or thermoelectric cooling is provided during the actual tissue coagulation procedure. Those known arrangements are intended for introduction into body cavities by way of natural accesses.

PCT application WO 00/36985 which was published after the relevant date discloses an electrode arrangement of that kind, in which two bar profile members are in the form of solid profile members and between them a spacer element which preferably comprises optical waveguides. Integration of the optical waveguides between the two bar profile members is however complicated and expensive. In addition the supply of fluids, in particular flushing fluids or cooling fluids, and/or sucking away body fluids which occur at the treatment location, is complicated and expensive.

SUMMARY OF THE INVENTION

Therefore the object of the invention is to develop an electrode arrangement of the kind set forth in the opening part of this specification in such a way that the arrangement is simple to produce and permits easy access from the exterior to the treatment location for treatment fluids or for sucking away body fluids.

In accordance with the invention, in the electrode arrangement of the kind set forth in the opening part of this specification, that object is attained in that at least one bar profile member is in the form of a hollow profile member.

The advantages of the invention are that simple manufacture of the electrodes is embodied by using standard profile members of conductive metal, in the form of a hollow profile member or solid profile member, wherein at least one bar profile member is in the form of a hollow profile member and therefore on the one hand increases the strength of the carrier while on the other hand it permits access to the treatment location for optical waveguides, treatment fluids etc. or for sucking away body fluids. The use of suitable bar profile members which are a component part of the carrier and which with a bare peripheral portion form a respective electrode implements various advantageous functions of the electrode arrangement. Thus the bar profile members are an integral component part of the carrier, in addition they embody in the longitudinal direction a respective electrode and—when being in the form of a hollow profile member—they can also be used to permit material transport from the distal end of the carrier outwardly, in a simple fashion.

In accordance with a preferred embodiment of the invention all bar profile members are in the form of a hollow profile member and can be of any cross-section, for example also a round cross-section. If three or more hollow profile members are used, a plurality of hollow passages are thus advantageously embodied, which permit material transport from the tip of the electrode arrangement to the exterior. Preferably each bar profile member has a bare metal outer portion as an electrode. If three or more bar profile members form the carrier, the overall diameter of the carrier is admittedly increased in that way, but the electromagnetic HF-field which is formed upon application of the HF-ac voltage between the electrodes extending in the longitudinal direction is also uniformly distributed at the outer periphery—in the peripheral direction.

In accordance with a particularly preferred embodiment of the invention two adjacent bar profile members are closed at their distal front ends and have through openings which connect the two hollow passages of the bar profile members together for the circulation of fluids, for example cooling fluid or predeterminedly temperature-controlled fluids.

In a preferred embodiment of the invention it is possible to use the hollow passage of a hollow bar profile member in order to position there on the one hand more likely displaceably from the proximal end of the electrode arrangement or fixedly an optical waveguide for positionally checking the distal end of the electrodes. For that purpose the hollow passage is open at the distal end and the optical waveguide outputs light at the distal end or receives reflected light and carries it back to the proximal end.

In that case the light sources used are laser or high-power diodes for the visible wavelength range which can preferably be fitted in the surgical instrument to which the electrode arrangement is releasably or fixedly coupled.

In accordance with a further preferred embodiment of the invention the spacer element is uniform over the entire length of the bar profile members and has at least one hollow passage which extends over the entire length of the electrode arrangement and which is open or closed at the distal end of the electrode arrangement. It is possible to arrange in such a hollow passage for example a temperature sensor which measures the tissue temperature at the distal end of the electrode arrangement and delivers suitable measurement values by way of lines towards the proximal end of the electrode arrangement.

Preferably each bar profile member with a predetermined metallically exposed peripheral portion forms an electrode extending in the longitudinal direction of the carrier. Preferably a spacer element between the bar profile member uniformly fills the intermediate space between the mutually oppositely disposed peripheral portions of the bar profile members in homogenous fashion. The spacer element in this embodiment is implemented either by an adhesive or a plastic casting material and holds the bar profile members in lively relationship firmly together, wherein the free electrodes are free of insulating material and are directed outwardly towards the tissue. The carrier can be either of a bipolar or a tripolar or a quadripolar structure, that is to say with two, three or four electrodes, which are electrically insulated from each other, extend in the longitudinal direction of the carrier and can be fed with a high-frequency ac voltage.

In accordance with a particularly preferred embodiment of the invention all bar profile members are in the form of solid profile members and are held together by an insulating spacer element. The bar profile members and the spacer element or elements together form an overall cross-section of the electrode arrangement, which preferably corresponds to a circular cross-section.

Advantageous developments of the invention are characterized by the features of the appendant claims.

BRIEF DESCRIPTION OF THE DRAWINGS

Embodiments of the invention are described in greater detail hereinafter with reference to the drawing in which:

FIG. 1 is a view in longitudinal section through a first embodiment of a bipolar electrode arrangement, FIG. 2 is a view in cross-section through the arrangement of FIG. 1, FIG. 3 is a view in longitudinal section through a second bipolar embodiment of the electrode arrangement.

DETAILED DESCRIPTION OF A PREFERRED EMBODIMENT

Figure 4:
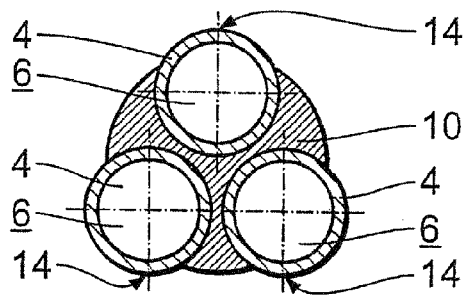
FIG. 4 is a view in cross-section through a tripolar embodiment of the electrode arrangement.

FIGS. 1 and 2 show a first embodiment of a bipolar electrode arrangement in longitudinal section and cross-section. In FIGS. 1 and 2 two round hollow profile members 4 of metal are arranged in mutually superposed relationship at a small spacing and together with a spacer element 10 provided between the hollow profile members 4 form a carrier 2 which on each hollow profile member 4 has an electrode 14 which extends in the longitudinal direction of the carrier 2 and which are connectable at the proximal end at which the electrode arrangement is coupled to a suitable surgical instrument. The hollow profile members 4 each have a respective hollow passage 6 which is open at the distal end 3 of the electrode arrangement, that is to say it has a respective opening 8. The two hollow profile members 4 converge to a tip 9 at the distal end 3. The electrodes which in use of the arrangement come into contact with the human or animal body tissue are formed by way of a respective predetermined exposed metallic peripheral portion 14 of a profile member 4. As the mutually opposite peripheral portion of the hollow profile members 4 the two hollow profile members 4 are connected together by means of an insulating spacer element 10, for example by means of a plastic profile member which extends uniformly over the entire electrode length. In the hollow passages 6 treatment fluids can be fed to the treatment location or body fluids can be withdrawn from the treatment location or optical waveguides can be fitted therein, which can light up the treatment location. The optical waveguide can be provided either fixedly or longitudinally displaceably in a hollow passage 6.

FIG. 3 shows a second embodiment of a bipolar electrode arrangement which substantially corresponds to the embodiment of FIGS. 1 and 2, but in which the two hollow passages 6 of the hollow profile members are closed at the distal end 3 by means of closure portions. In comparison there are through openings 7 between the hollow passages 6 of the two hollow profile members 4 and they permit a counter-flow circulation of a temperature-controlled fluid from the proximal end of the electrode arrangement to the distal end 3 and back again to the proximal end.

FIG. 4 shows a tripolar embodiment of the electrode arrangement in which three hollow profile members—disposed at the corners of a triangle with their longitudinal axes as viewed in cross-section—extend in the longitudinal direction of the carrier and form the electrode arrangement. The hollow profile members 4 each have a respective hollow passage 6 which can be open or closed at the distal end of the electrode arrangement. The hollow profile members 4 comprise metal and have an exposed metallic peripheral portion which extending in the longitudinal direction forms the electrodes 14. There is a respective electrode 14 for each hollow profile member 4, and overall the arrangement therefore forms three electrodes 14 which extend in the longitudinal direction and to which the HF-ac voltage can be proximally applied, wherein two of the hollow profile members can also be electrically connected together, but alternatively they can be at different ac voltages. The three hollow profile members 4 are connected together by means of an insulating spacer element 10. The spacer element 10 extends at the mutually adjacent peripheral portions of the hollow profile members 4, whereas the exposed metallic peripheral portions 14 are not covered with insulating material of the spacer element 10.

Figure 5:
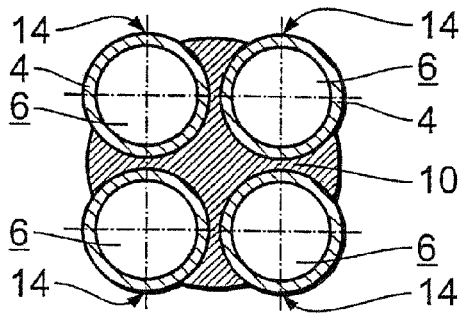
FIG. 5 is a view in cross-section through a quadripolar embodiment of the electrode arrangement.

FIG. 5 shows a view in cross-section through a quadripolar embodiment of the electrode arrangement, in which four metallic hollow profile members 4 of round cross-section are connected together in insulating relationship and are fixed to each other, in the longitudinal direction, by means of one or more successively disposed spacer elements 10. External exposed metallic peripheral portions of the hollow profile members 4 each form a respective electrode 14, in total therefore four electrodes 14 which extend in the longitudinal direction and which in use of the electrode arrangement come into contact with the human or animal body tissue and between which the electromagnetic field required for electrothermal coagulation is formed when an HF-ac voltage is proximally applied.

Figure 6:
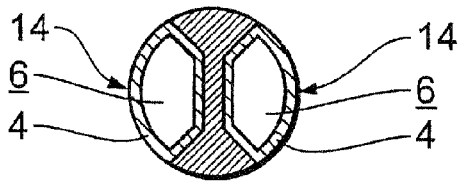
FIG. 6 is a view in cross-section through a third bipolar embodiment of the electrode arrangement.
Figure 7:
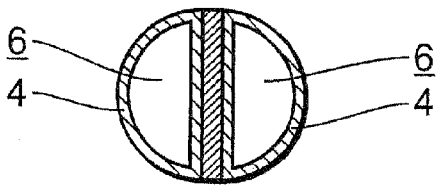
FIG. 7 is a view in cross-section through a fourth bipolar embodiment of the electrode arrangement.

FIGS. 6 through 10 show further embodiments of the bipolar electrode arrangement which are characterized in that the peripheral contour of the cross-section of the electrode arrangement is round. In FIGS. 6 and 7 the bar profile members are two hollow profile members 4 of a polygonal cross-section or a semicircular cross-section which are insulated from each other by means of a uniform spacer element 10. The hollow passages 6 serve to receive sensors or optical waveguides or serve as passages for treatment or temperature-control fluid. The externally disposed bare metallic peripheral portions serve as electrodes and extend in the longitudinal direction of the arrangement.

Figure 8:
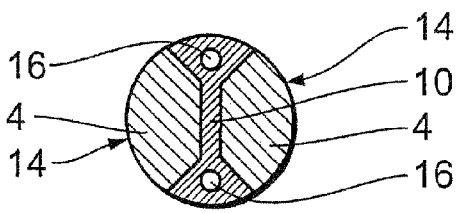
FIG. 8 is a view in cross-section through a fifth bipolar embodiment of the electrode arrangement.
Figure 10:
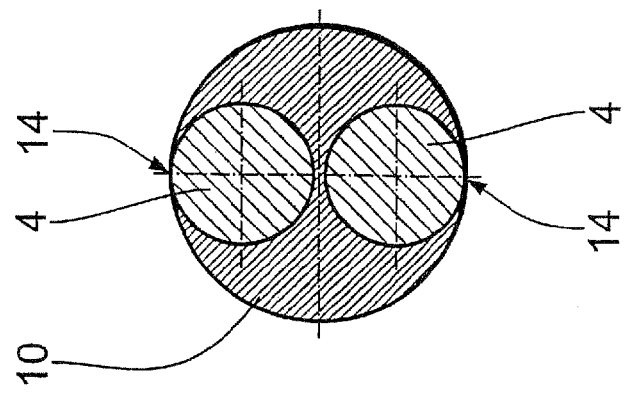
FIG. 10 is a view in cross-section through the electrode arrangement shown in FIG. 9.
Figure 9:
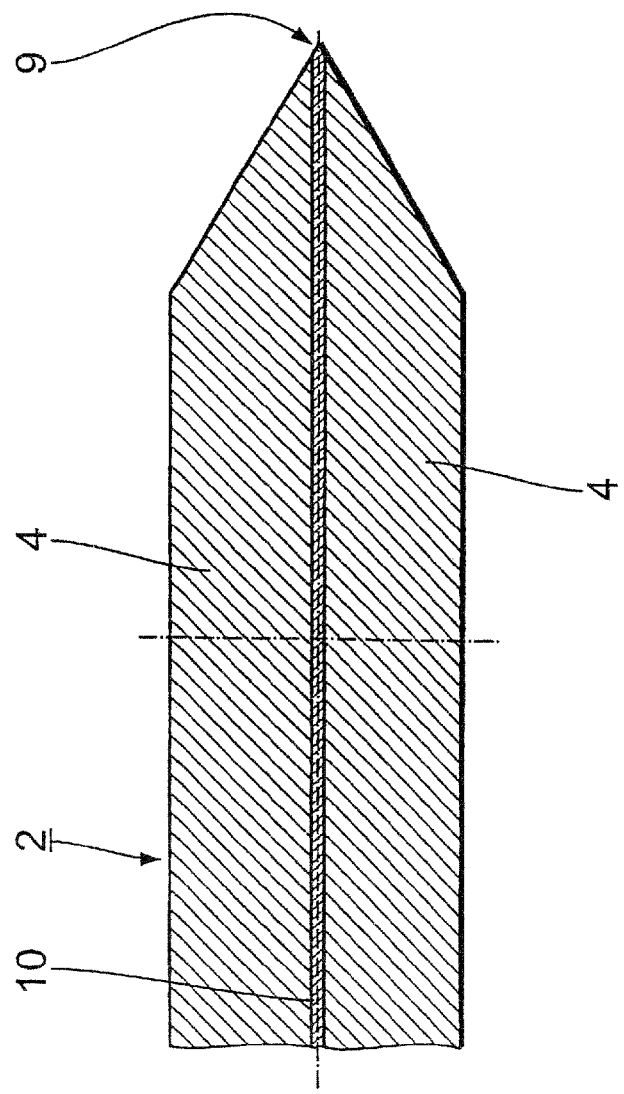
FIG. 9 is a view in longitudinal section through a sixth bipolar embodiment of the electrode arrangement.

FIGS. 8, 9 and 10 also show bipolar electrode arrangements in which however two solid profile members extend in the longitudinal direction of the carrier, that is to say they do not have any hollow passages. Inserted between the metallic solid profile members 4 is a spacer element 10 of insulating material, which fixedly connects the two solid profile members 4 together and—in the embodiment shown in FIG. 8—has two hollow passages 16 which extend in the longitudinal direction from the proximal end of the electrode arrangement to the distal end. The exposed metallic peripheral portions 14 form the two electrodes which extend in strip form in the longitudinal direction and which come metallically into contact with the body tissue when the electrode arrangement is in use. The embodiment illustrated in FIGS. 9 and 10 includes two solid profile members 4 which are of round cross-section and which are fixedly connected together by way of the spacer element 10. The external contour of the electrode arrangement is approximately round while the distal end 3 has a tip 9.

What is claimed is:

1. An electrode arrangement for a surgical instrument for the electrothermal coagulation of human or animal tissue, comprising:
an elongate carrier; and
a plurality of self-supporting metal bar profile members, capable of being connected to an ac voltage and having electrodes, wherein said metal bar profile members are an integral component part of the carrier and which extend side-by-side in the longitudinal direction of the carrier and which are connected together by means of at least one insulating spacer element such that said at least one insulating spacer element is arranged between said bar profile members and extends uniformly over an entire length thereof, and wherein each of said plurality of metal bar profile members exhibit a bare peripheral portion forming a respective electrode of said electrodes that is capable of making contact with tissue, characterized in that at least one bar profile member is in the form of a hollow profile member having a hollow passage closed at a distal end, and wherein said bare peripheral portion extends at least in said longitudinal direction.

2. The electrode arrangement of claim 1, wherein:
each said bar profile member is in the form of a hollow profile member.

3. The electrode arrangement of claim 2, wherein:
each said bar profile member has a round cross-section.

4. The electrode arrangement of claim 3, wherein:
the bar profile members have mutually adjacent cross-sectional regions with the insulating spacer members arranged therebetween.

5. The electrode arrangement of claim 4, wherein:
the at least one spacer element fills an intermediate space between mutually opposite peripheral portions of the bar profile members.

6. The electrode arrangement of claim 5, wherein:
through passage openings are provided between adjacent hollow passages for the circulation of fluids.

7. The electrode arrangement of claim 5, wherein:
the bar profile members together with the at least one insulating spacer element form an approximately round cross-section.

8. The electrode arrangement of claim 5, wherein:
at least one hollow passage is provided in the at least one insulating spacer element, the hollow passage extending from a proximal end to a distal end thereof.

9. The electrode arrangement of claim 5, wherein:
the distal end of the electrode arrangement is pointed.

10. The electrode arrangement of claim 5, wherein:
the electrodes occupy a predetermined peripheral portion of the bar profile members and the remaining peripheral portion of the bar profile members is covered by the insulating spacer element.

11. The electrode arrangement of claim 5, wherein:
the bar profile members together with the at least one insulating spacer element form an approximately round cross-section.

12. The electrode arrangement of claim 5, wherein:
the distal end of the electrode arrangement is rounded.

13. The electrode arrangement of claim 1, wherein:
each said bar profile member has a round cross-section.

14. The electrode arrangement of claim 1, wherein:
the bar profile members have adjacent cross-sectional regions with the insulating spacer elements arranged therebetween.

15. The electrode arrangement of claim 1, wherein:
a hollow passage of at least one said bar profile member is open at a distal end and is in the form of a fluid passage whose proximal end is connectable to a fluid source.

16. The electrode arrangement of claim 15, wherein:
through passage openings are provided between adjacent hollow passages for the circulation of fluids.

17. The electrode arrangement of claim 1, wherein:
at least one hollow passage is provided in the at least one insulating spacer element, the hollow passage extending from a proximal end to a distal end thereof.

18. The electrode arrangement of claim 1, wherein:
the distal end of the electrode arrangement is pointed.

19. The electrode arrangement of claim 1, wherein:
the distal end of the electrode arrangement is rounded.

20. The electrode arrangement of claim 1, wherein:
the electrodes occupy a predetermined peripheral portion of the bar profile members and the remaining peripheral portion of the bar profile members is covered by the insulating spacer element.

21. The electrode arrangement of claim 1, wherein:
the electrode arrangement has an approximately circular cross-section.

22. The electrode arrangement of claim 1, wherein:
a distal end thereof terminates in a point.

* * * * *

UNITED STATES PATENT AND TRADEMARK OFFICE
CERTIFICATE OF CORRECTION

| | |
|---|---|
| PATENT NO. | : 7,666,183 B2 |
| APPLICATION NO. | : 10/296189 |
| DATED | : February 23, 2010 |
| INVENTOR(S) | : Kai Desinger |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1092 days.

Signed and Sealed this

Seventh Day of December, 2010

David J. Kappos
*Director of the United States Patent and Trademark Office*